(12) United States Patent
Tatar et al.

(10) Patent No.: US 9,702,816 B2
(45) Date of Patent: Jul. 11, 2017

(54) OPTICAL FIBER SENSOR USED FOR OIL CONDITIONING MONITORING

(71) Applicant: AKTIEBOLAGET SKF, Göteborg (SE)

(72) Inventors: Florin Tatar, Delft (NL); Defeng Lang, Delft (NL)

(73) Assignee: AKTIEBOLAGET SKF, Gothenburg (SE)

( * ) Notice: Subject to any disclaimer, the term of this patent is extended or adjusted under 35 U.S.C. 154(b) by 0 days.

(21) Appl. No.: 15/105,397

(22) PCT Filed: Dec. 17, 2013

(86) PCT No.: PCT/EP2013/076791
§ 371 (c)(1),
(2) Date: Jun. 16, 2016

(87) PCT Pub. No.: WO2015/090359
PCT Pub. Date: Jun. 25, 2015

(65) Prior Publication Data
US 2017/0045445 A1    Feb. 16, 2017

(51) Int. Cl.
| | | |
|---|---|---|
| *G01N 21/3577* | (2014.01) | |
| *G01J 3/42* | (2006.01) | |
| *G01N 33/28* | (2006.01) | |
| *G01N 21/3554* | (2014.01) | |
| *G01N 21/359* | (2014.01) | |
| *G01N 21/45* | (2006.01) | |

(Continued)

(52) U.S. Cl.
CPC ........ *G01N 21/3577* (2013.01); *G01J 3/0218* (2013.01); *G01J 3/42* (2013.01); *G01N 21/359* (2013.01); *G01N 21/3554* (2013.01); *G01N 21/45* (2013.01); *G01N 21/8507* (2013.01); *G01N 33/2847* (2013.01); *G01N 33/2888* (2013.01); *G01N 2201/0846* (2013.01)

(58) Field of Classification Search
CPC .......... G01J 1/58; G01J 3/42; G01N 21/3577
See application file for complete search history.

(56) References Cited

U.S. PATENT DOCUMENTS

| | | | |
|---|---|---|---|
| 3,392,623 A | 7/1968 | Walker et al. | |
| 5,712,934 A * | 1/1998 | Johnson .............. | G01F 23/2927 250/339.11 |

(Continued)

FOREIGN PATENT DOCUMENTS

| | | |
|---|---|---|
| DE | 3712879 A1 | 11/1988 |
| EP | 2009438 A1 | 12/2008 |
| WO | 2012058716 A1 | 5/2012 |

*Primary Examiner* — David Porta
*Assistant Examiner* — Faye Boosalis
(74) *Attorney, Agent, or Firm* — Bryan Peckjian; SKF USA Inc. Patent Dept.

(57) ABSTRACT

A detector for oil condition monitoring includes an optical fiber having a first end and a second end having an end face. A sensor body has a gap in which a sample of the oil may be received and a reflecting surface, the second end of the optical fiber being embedded in the sensor body and having an end face spaced from the reflecting surface across the gap. Light emitted from the optical fiber can pass through the sample of oil and be reflected by the reflecting surface back into the optical fiber. By interferometry of the respective signals, the condition of the oil can be determined.

15 Claims, 2 Drawing Sheets

(51) Int. Cl.
*G01N 21/85* (2006.01)
*G01J 3/02* (2006.01)

(56) References Cited

U.S. PATENT DOCUMENTS

2009/0185187 A1  7/2009  Crist et al.
2011/0249257 A1  10/2011 Wildschuetz et al.
2012/0112072 A1  5/2012  Jones et al.

* cited by examiner

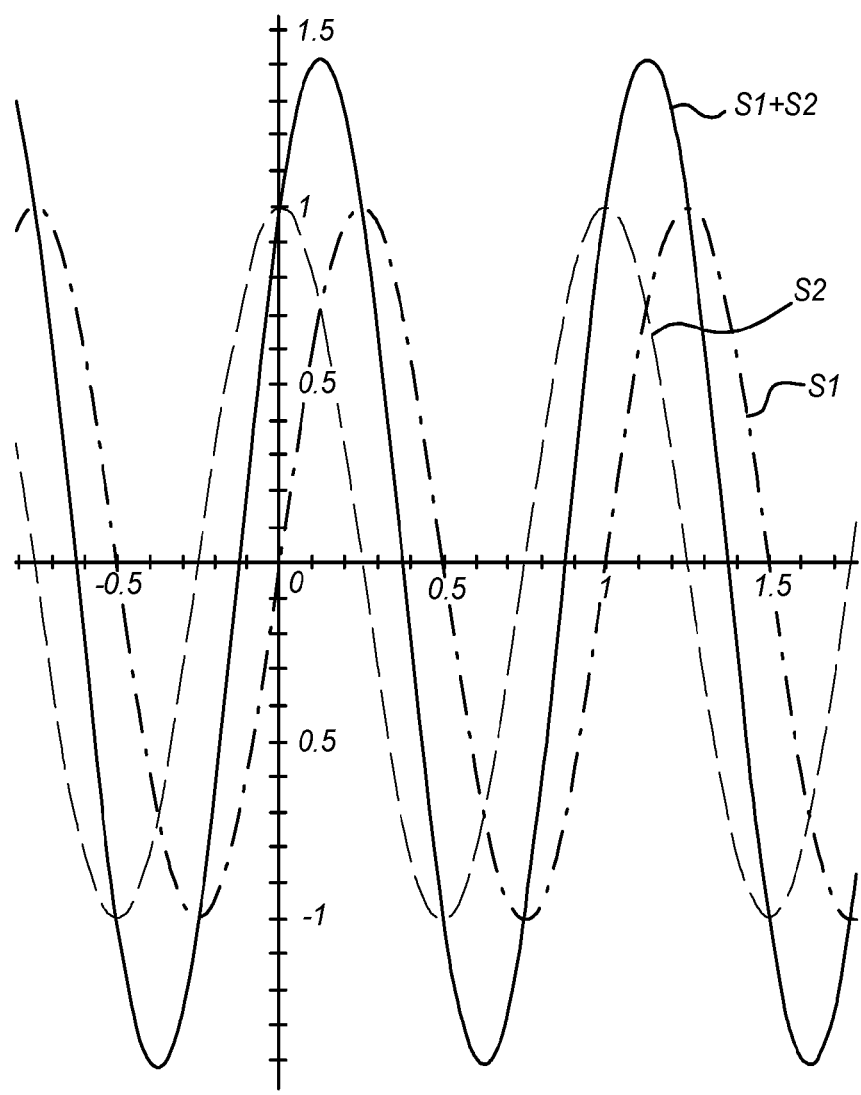

OPTICAL FIBER SENSOR USED FOR OIL CONDITIONING MONITORING

CROSS-REFERENCE

This application is the U.S. national stage of International Application No. PCT/EP2013/076791 filed on Dec. 17, 2013, the contents of which are fully incorporated herein by reference.

BACKGROUND OF THE INVENTION

1. Field of the Invention

The present invention relates to oil condition monitoring and in particular, to a sensor for detecting the presence and amount of water in oil or like substances. The invention also relates to a method of monitoring the presence of water in oil.

2. Description of the Related Art

Optical sensors have been used for oil condition monitoring for determining the presence of debris or otherwise monitor deterioration of a lubricant. Such devices may operate by shining light through a small gap and analysing the transmitted light with a suitable optical sensor. Alternative sensors may make use of scattering of light and may operate over different frequencies including outside of the visible range. Oil condition monitoring may be significant in providing feedback in advance of likely failure of a lubricant system. Action may be taken to perform maintenance or otherwise renew the lubricant.

Water in oil is of considerable concern to many mechanical systems. Minimal amounts of water may be absorbed by the oil during use, either from the atmosphere or by direct ingress of water into the system. As long as this water is in the absorbed state and the oil is unsaturated, the concern is minimal. Nevertheless, as the concentration of water approaches the saturation level, emulsified and free water may occur, which can be highly detrimental, especially if exposure is prolonged. In bearings, the incompressibility of water relative to the oil can result in disruption of the oil film leading to excessive wear. Just one percent water in oil can reduce the life expectancy of a bearing by as much as 90 percent. For ball or rolling element bearings, the localized pressure generated can cause spontaneous vaporization of the water, leading to erosive wear such as micropitting. The saturation level of water in oil may vary widely according to temperature and the type of oil and can range from 10 ppm to even 10000 ppm. Existing sensors capable of measuring the presence of water (free and dissolved) include capacitive sensors and Karl Fischer titration sensors. Both of these methods require considerable time for the sensor to reach equilibrium and are not ideal for rapidly changing conditions. Spectral analysis using Fourier Transform Infrared Spectroscopy (FTIR) has been used but is a relatively complex and costly procedure requiring calibration of the sensor relative to the spectrum produced with fresh oil.

A sensor has been proposed in co-pending application No PCT/EP2012/075437 by which water in oil can be conveniently detected and whereby calibration of the device is simplified. An alternative arrangement has been proposed in co-pending application No PCT/EP2012/075395 in which use of cost-effective LED's is proposed. The contents of these documents are incorporated herein by reference in their entirety. In both cases, the sensor has a gap for transmission of light between an emitter and receiver through a sample of the oil. The light passing through the oil from the emitter is detected at the receiver and a light signal representative of the light detected is analysed to determine an amount of signal fluctuation. A step change in the signal fluctuation is indicative of saturation of the oil.

Although the proposed devices have been found to function correctly, it would be desirable to both improve on their sensitivity to external factors and simplify their construction.

BRIEF SUMMARY OF THE INVENTION

According to the invention there is provided a detector for oil condition monitoring comprising an optical fibre having a first end and a second end having an end face, a sensor body, having a gap in which a sample of the oil may be received and a reflecting surface, the second end of the optical fibre being embedded in the sensor body and having an end face spaced from the reflecting surface across the gap, whereby light emitted from the optical fibre can pass through the sample of oil and be reflected by the reflecting surface back into the optical fibre. As a result of the proposed configuration, the sensor is less sensitive to external factors than previous designs. Optical fibres used in sensing configurations are rather sensitive to bending. As the bending curvature of the fibre changes, so too does the amplitude of a signal passing through the fibre. As a consequence for existing sensing systems, the whole system must be free from geometry change during operation. According to the presently claimed detector, the signal path includes a mirror and light interference between a first light signal reflected internally by the fibre and a second light signal reflected by the mirror can be monitored. In this manner, amplitude signal changes due to changes in the fibre curvature are eliminated.

In a preferred embodiment of the invention, the gap between the end face and the reflecting surface is less than 1 mm, preferably less than 0.5 mm and most preferably around 0.2 mm. The actual gap may be chosen according to the nature of the oil being treated. Since the signal must pass the gap twice before re-entering the fibre, the gap in the presently claimed configuration may need to be around half of the width of a corresponding gap when the sensor is opposed to the light source.

The sensor body may be manufactured of any material, including metals, plastics and the like, in particular those suitable for protecting it mechanically and chemically from external influences. Most preferably, the sensor body is made of ceramic material such as is conventionally used for ferrules for fibre-optic connectors.

According to a further important aspect of the invention, the optical fibre may be potted in the sensor body in a rigid fashion to avoid any movement or vibration being transmitted thereto. Preferably, the fibre is potted in the sensor body over a length of at least 5 mm.

The detector is intended for operation with a suitable light source and may further comprise such a light source coupled to the first end of the optical fibre. Most preferably, the light source is a laser source. The laser source may operate at frequencies ranging from 850 nm to 1750 nm.

Any suitable detection arrangement may be used to interrogate the sensor. Most preferably, the detector further comprises an interferometer coupled to the first end of the optical fibre and arranged to compare a first light signal reflected internally by the end face with a second light signal reflected by the reflecting surface. The first light signal that is reflected by the end face of the fibre is used in the interferometer as the reference signal. The second light signal that is reflected at the reflecting surface is the measurement signal, which is added to reference signal in an interfering manner. Any amplitude change caused by fibre bending will influence both reference signal and measurement signal in a fixed proportional way. In this manner the amplitude change caused by fibre bending becomes a known factor. An actual amplitude change that represents the oil water saturation level can be calculated by removing the known factor. The detector is thus not restricted to any particular geometry and movement can take place without upsetting the calibration.

The skilled person will be well aware of appropriate ways in which a light source and interferometer may be coupled into the optical fibre. In one preferred configuration, the light source and the interferometer may be coupled via an optical switch. One such optical switch may be in the form of a semi-reflective mirror or prism. Other similar beam splitters may also be used.

The invention also relates to a method of condition monitoring of oil in a mechanical system, comprising positioning an end face of an optical fibre in spaced relation to a reflecting surface, providing a sample of the oil to bridge the gap between the end face and the reflecting surface, passing light through the optical fibre towards the end face, whereby a first portion of the light is internally reflected by the end face as a first light signal and a second portion of the light is transmitted through the oil and reflected by the reflecting surface back into the optical fibre as a second light signal and analysing the first and second light signals to determine an amount of attenuation of the second light signal due to the presence of water in the oil.

In one embodiment, the light may be chosen to have a primary frequency calibrated to the gap such that the first and second light signals interfere constructively with each other. In other words, the wave length of the light and the gap width are accurately chosen such that the waves are in phase. It will be understood that although reference is given to a choice of frequency, it may also be the gap or position of the end face with respect to the reflecting surface precise that is chosen to match the frequency.

In another embodiment of the invention, the step of analysing the first and second light signals comprises scanning the frequency spectrum to identify a maximum at which the first and second light signals add together. Use of a scanning optical spectrometer can allow the system to determine the frequency at which the light signals are in phase. At this point, the relative amplitude variation can be better compared with an expected amplitude variation due to the presence of dissolved water. It will be understood that a lower combined signal may be due to either to attenuation of the second light signal or to the fact that the signals are out of phase and cancelling each other out. By scanning the frequency signal for the location at which the signals are in phase, this uncertainty may be avoided. It will be understood that the scan may be limited to the region where the light signals are expected to be in phase and that this may vary only slightly once established.

Preferably, the step of analysing the first and second light signals comprises determining the relative attenuation of the second light signal with respect to the first light signal and comparing the relative attenuation with predetermined values representative of the saturation level of water in the oil. The detector may be calibrated in advance for oil having predetermined saturation levels. The values may be stored as look-up tables in a suitable memory and extrapolation between these values may be used to determine a momentary saturation level.

The detector may also be used to identify the point at which free water becomes present i.e. 100% saturation. It has been observed that a significant change in signal characteristic is to be observed at the point at which free water appears in the oil. Below the saturation level, the amplitude of the second light signal is relatively stable and only steadily decreases with increasing absorbed water content. As the amount of water approaches saturation, the second light signal becomes highly unstable and may appear noisy. Without wishing to be bound by theory, it is believed that bubbles of free water are formed within the oil in a manner similar to cavitation or boiling of a liquid. As these bubbles pass the sensor, they disturb the signal, effectively leading to greater absorption of the light and a lower second light signal. A significant advantage of the above effect is that the detector can be easily calibrated in-situ to the saturation level, without requiring knowledge of either the oil or sensor characteristics. Additionally, the sensor can provide real-time results with negligible delay in identifying the presence of free water in the oil.

Determination of the onset of free water and the step change in fluctuation of the signal can be realised in many ways as will be evident to the skilled person. This may be determined visually and manually on reviewing a data stream record of the light signal. Alternatively and preferably, the method may be carried out by a signal processor using an appropriate algorithm. In one embodiment of the invention, the amount of fluctuation may be determined by measuring a maximum peak to peak variation of the light signal within a sampling period. The sampling period may be chosen depending on various factors, including the sampling rate at which measurements of the light signal are taken and also based on physical factors such as the flow rate of the oil being monitored. It will be understood that the sampling period will include at least two samples, preferably at least four samples and more preferably at least 10 samples.

Although light across a range of frequencies may be used to carry out the invention, preferably the light comprises infra red light in the range 850 nm to 1750 nm.

The process is preferably carried out using a controller, which may be any appropriate processing device such as a computer or dedicated microprocessor. In addition to other control tasks, the controller is preferably arranged to determine when the fluctuation of the light signal exceeds the preset value. In particular the controller may carry out signal analysis, sampling and filtering as described above.

The skilled person will understand that the sensor of the present invention may be implemented in a number of different situations where water in oil is to be recorded. Preferably, the optical sensor is located in an oil supply line to a mechanical system. The mechanical system may be a motor, a gear, a bearing, a journal, a cam or a complex system comprising one or more of the above.

BRIEF DESCRIPTION OF THE DRAWINGS

The features and advantages of the invention will be appreciated upon reference to the following drawing of an exemplary embodiment, in which:

FIG. 2 shows a plot of the light signals received by the spectroanalyzer.

DESCRIPTION OF ILLUSTRATIVE EMBODIMENTS

Figure 1:
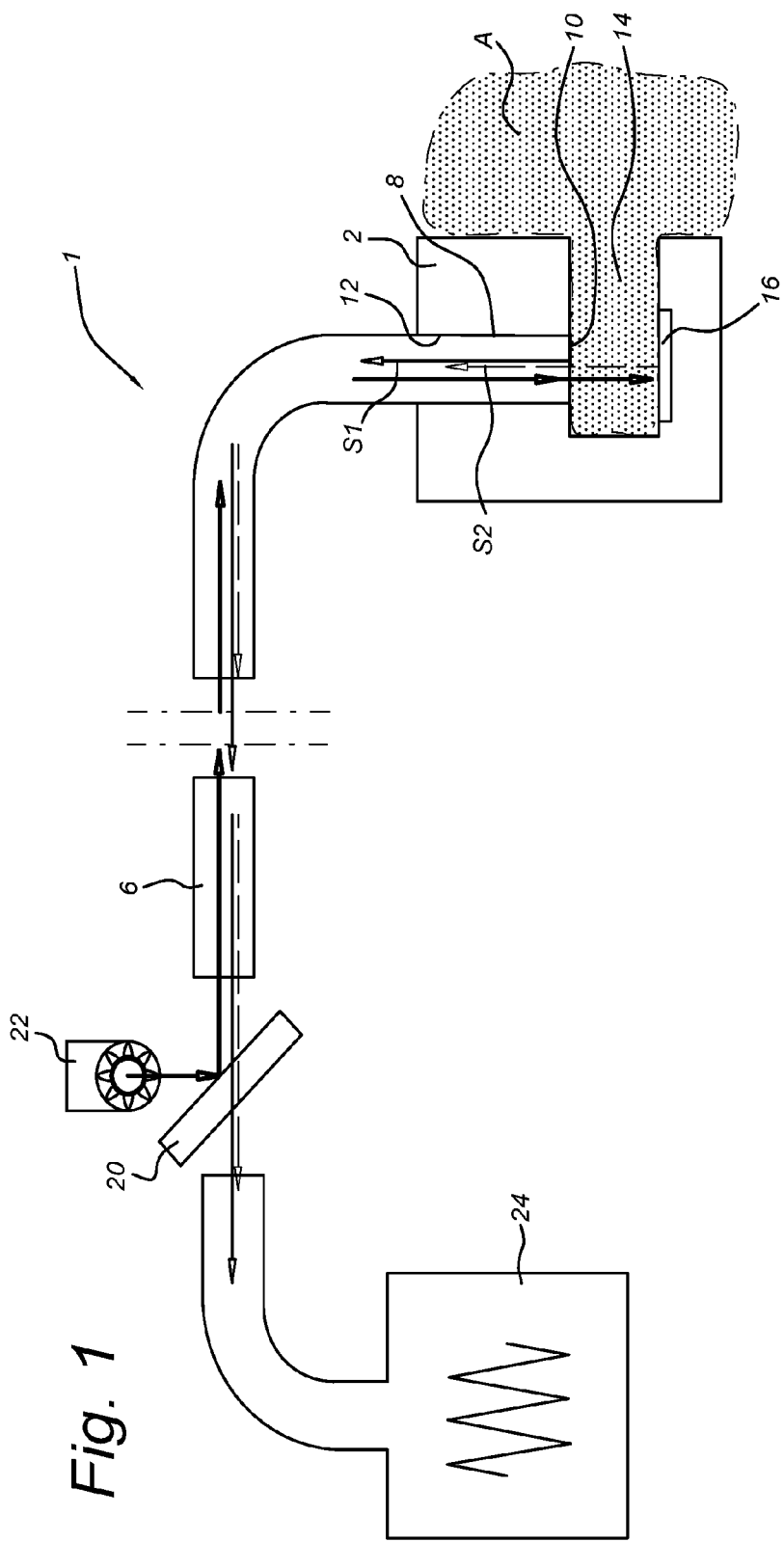
FIG. 1 shows a schematic view of a system according to the present invention.

FIG. 1 shows a schematic view of a detector 1 for oil condition monitoring according to the invention. The detector 1 comprises a sensor body 2 and an optical fibre 4. The optical fibre 4 has a first end 6 and a second end 8 having a semi-reflective end face 10. This may be achieved with an appropriate semi-reflective mirror coating. The second end 8 is embedded in a channel 12 through the sensor body 2 such that the end face 10 is coincident with a gap 14 extending through the sensor body 2. At an opposite side of the gap 14 from the channel 12, facing the end face 10 of the optical fibre 4 is a reflecting surface 16.

At its second end 8, the optical fibre 4 is coupled through a semi-reflective mirror 20 to a laser source 22 and a spectroanalyzer 24. The semi-reflective mirror 20 acts as an optical switch between the laser source 22 and the spectroanalyzer 24 as described further in detail below.

In use, the sensor body 2 is located within a mechanical system (not shown) such that oil A is received in the gap 14. Light L from the laser source 22 is coupled into the fibre 4 and guided through the optical fibre 4 to exit at the end face 10. A portion of the light L is reflected internally by the semi-reflective surface of the end face 10 and returns through the optical fibre as first light signal S1. The remainder of the light L passes into and through the oil A in the gap 14 and impinges on the reflecting surface 16, which reflects it back across the gap 14 and into the second end 8 of the optical fibre 4 as second light signal S2.

The first and second light signals S1, S2 are transmitted through the optical fibre 4 and the semi-reflective mirror 20 to the spectroanalyzer 24. The spectroanalyzer 24 is operated to scan the frequency spectrum and determine the frequency at which the signals S1, S2 constructively interfere. In general, once determined, this frequency will remain relatively stable for a given configuration and can be identified as a maximum in the combined signal S1+S2.

The first light signal S1 is used as the reference signal. The second light signal S2 is added to the first light signal S1 to ensure interference way. Any amplitude changes caused by the fibre 4 bending will influence both signals S1 and S2 in a fixed proportional way. In this way amplitude changes caused by fibre bending becomes a known factor. The actual amplitude change that represents an oil in water saturation level can be calculated by removing the known factor. The measurement system is therefore not restricted to any fixed geometry.

FIG. 2 shows a plot of the light signals S1 and S2 and the combined signal S1+S2. When the signals S1 and S2 are in phase, the combined signal S1+S2 is at a maximum value, being the sum of the two signals. Under normal conditions, the signal S1 will be relatively constant, since its reflection is independent of the oil condition. The signal S2 is attenuated according to the amount of water absorbed within the oil. Signal S2' represent a sample taken in which water in the oil A has caused attenuation of the signal S2'. While the relative saturation of water in oil is below 100%, the change in attenuation of S2' with increasing water content is relatively linear. Values for the attenuation may be provided in advance and stored in a look-up table in an appropriate memory (not shown). The measured value can then be compared with the precalibrated value to determine the relative saturation of the oil. In this context, relative saturation is understood to be the absolute water content compared to the maximum water content of the oil at which separation takes place.

It is furthermore noted that during use, any variation in the temperature of the oil can cause a variation in the width of the gap 14 due to expansion of the ferrule. This will result in a phase delay for the second light signal with respect to the first light signal. The temperature of the oil may thus also be taken into consideration during analysis by separately evaluating both the phase and the amplitude variation between the first and second signals.

Thus, the invention has been described by reference to the embodiment discussed above. It will be recognized that this embodiment is susceptible to various modifications and alternative forms well known to those of skill in the art without departing from the spirit and scope of the invention. In particular, for implementation in a mechanical system, the detection cell may be located in an oil supply line whereby a portion of the oil supply passes through the gap. Furthermore, the analysis of the signals may take place on a personal computer or a dedicated controller or microprocessor which may be located in-situ or remotely. Accordingly, although specific embodiments have been described, these are examples only and are not limiting upon the scope of the invention.

The invention claimed is:

1. A detector for oil condition monitoring, the detector comprising:
    an optical fibre having a first end and a second end, wherein the second end comprises an end face provided with a semi-reflective coating;
    a sensor body comprising a gap that receives a sample of the oil and a reflecting surface,
    wherein the second end of the optical fibre is embedded in the sensor body and having the end face spaced from the reflecting surface across the gap,
    wherein a first portion of light emitted from the optical fibre is reflected internally by the semi-reflective coating of the end face back through the optical fibre,
    wherein a second portion of the light emitted from the optical fibre passes through the end face and the sample of the oil and is reflected by the reflecting surface back into the optical fibre; and
    an interferometer coupled to the first end of the optical fibre and configured to compare the first portion of the light reflected internally by the end face with the second portion of the light signal reflected by the reflecting surface.

2. The detector of claim 1, wherein the gap between the end face and the reflecting surface is less than 1 mm.

3. The detector according to claim 1, wherein the sensor body is made of ceramic material.

4. The detector according to claim 1, wherein the optical fibre is potted in the sensor body over a length of at least 5 mm.

5. The detector according to claim 1, further comprising a light source coupled to the first end of the optical fibre.

6. The detector according to claim 5, wherein the light source is an infra-red laser source.

7. The detector according to claim 1, where the light source and the interferometer are coupled via an optical switch.

8. The detector of claim 1, wherein the gap between the end face and the reflecting surface is less than 0.5 mm.

9. The detector of claim 1, wherein the gap between the end face and the reflecting surface is about 0.2 mm.

10. A method of condition monitoring of oil in a mechanical system, comprising:
    positioning an end face of an optical fibre in spaced relation across a gap of a sensor body to a reflecting surface of the sensor body, the end face comprising a semi-reflective coating;
    providing a sample of the oil to bridge the gap of the sensor body between the end face and the reflecting surface;

passing light through the optical fibre towards the end face, wherein a first portion of the light is internally reflected by the semi-reflective coating of the end face as a first light signal and, wherein a second portion of the light is transmitted through the end face and the sample of the oil and reflected by the reflecting surface back into the optical fibre as a second light signal; and analysing, by an interferometer coupled to the optical fibre, the first and second light signals to determine an amount of attenuation of the second light signal due to the presence of water in the oil.

11. The method according to claim 10, wherein the light has a primary frequency calibrated to the gap such that the first and second light signals constructively interfere with each other.

12. The method according to claim 10, wherein the step of analysing the first and second light signals includes scanning the frequency spectrum to identify a maximum at which the first and second light signals add together.

13. The method according to claim 10, wherein analysing the first and second light signals comprises determining the relative attenuation of the second light signal with respect to the first light signal and comparing the relative attenuation with predetermined values representative of the saturation level of water in the oil.

14. The method according to claim 10, wherein the light comprises infra-red light in the range 850 nm to 1750 nm.

15. The method according to claim 10, further comprising a controller adapted to analyse the light signals.

* * * * *